(12) United States Patent
Peterson et al.

(10) Patent No.: US 6,177,476 B1
(45) Date of Patent: Jan. 23, 2001

(54) NUTRITIONAL SUPPLEMENTS FOR REPLENISHING PLASMALOGENS

(75) Inventors: Andrew C. Peterson; Thaddeus P. Pruss, both of Madison, WI (US)

(73) Assignee: Clarion Pharmaceuticals Inc., Madison, WI (US)

( * ) Notice: Under 35 U.S.C. 154(b), the term of this patent shall be extended for 0 days.

(21) Appl. No.: 09/141,061

(22) Filed: Aug. 27, 1998

(51) Int. Cl.$^7$ .................................................. A61K 31/08
(52) U.S. Cl. .......................... 514/722; 514/715; 514/723
(58) Field of Search .................... 514/715, 722, 514/723

(56) References Cited

U.S. PATENT DOCUMENTS

| | | | |
|---|---|---|---|
| 3,294,639 | 12/1966 | Chalmers et al. | 167/65 |
| 4,465,869 | 8/1984 | Takaishi et al. | 568/672 |
| 4,505,933 | 3/1985 | Hörrmann | 514/693 |
| 4,687,783 | 8/1987 | Hörrmann | 514/693 |
| 5,173,511 | 12/1992 | Brohult et al. | 514/723 |
| 5,731,354 | 3/1998 | Pruss | 514/723 |

FOREIGN PATENT DOCUMENTS 1029610 5/1966 (GB).

OTHER PUBLICATIONS

Amon, U.; von Stebut, E.; Ramachers, U.; and Wolff, H.H. (1993); Influence of protein kinase C activation on basophils from patients with atopic dermatitis in comparison with nonatopic controls, *Dermatology*, 186:109–112.

Burgos, C.E.; Ayer, D.E.; and Johnson, A.R. (1987); A New, Asymmetric Synthesis of Lipids and Phospholipids, *J. Org. Chem.*, 52:4973–4977.

Das et al. (1992); Dietary Ether Lipid Incorporation Into Tissue Plasmalogens of Humans and Rodents, *Lipids*, 27(6):401–405.

Hermetter, A. and Paltauf, F. (1995); in "Phospholipids: Characterization, Metabolism, and Novel Biological Applications," Cevc, G., Paltauf, F., Eds.; pp. 260–273: AOCS Press, Champaign, Illinois.

Hirth, G.V. and Barner, R. (1982); Herstellung von 1–O–Octadecyl–2–O–acetyl–sn–glyceryl–3–phosphorychoin ('Platelet Activatiing Factor'), des Enantiomeren sowie einiger analoger Verbindungen, *Helv. Chim. Acta.*, 65:1059–1084.

Hirth, G.V.; Saroka, H.; Banwarth, W.; and Barner, R. (1983); Herstellung von 2–O–Acetyl–1–O–[ (Z) –9–octadecenyl ]–sn–glyceryl–3–phosphorylcholin (<<Oley-l–PAF>>), des Enantiomeren sowie einiger analoger, ungesättogter Verbindungen, *Helv. Chim. Acta.*, 66:1210–1240.

Horrocks (1972); in "Ether Lipids: Chemistry and Biology," Snyder, F. Ed., pp. 177–272.

Nunez and Clarke (1994); "the Bcl–2 Family of Proteins: Regulators of Cell Death and Survival," *Trends in Cell Biology*, 4:399–403.

Paltauf, F. (1994); Ether Lipids in biomembranes, *Chemistry and Physics of Lipids*, 74:101–13.

Reiss, D.; Beyer, K.; and Englemann, B. (1997); Delayed oxidative degradation of polyunsaturated diacyl phospholipids in the presence of plasmalogen phospholipids in vitro, *Biochem. J.*, 323:807–814.

Wanders et al. (1986); Age–related Differences in Plasmalogen Content of Erythorcytes from Patients with the Cerebro–hepato–renal (Zellweger) Syndrome: Implictions for Postnatal Detection of the Disease, *J. Inher. Metab. Dis.*, 9:335–342.

*Primary Examiner*—Marianne M. Cintins
*Assistant Examiner*—C. Delacroix-Muirheid
(74) *Attorney, Agent, or Firm*—Joseph T. Leone, Esq.; Salvatore R. Conte, Esq.

(57) ABSTRACT

A method of replenishing plasmalogens in mammals comprising treatment with a plasmalogen-replenishing-effective amount of one or more stantially pure monoethers of glycerols and their carboxylic acid ester derivatives of Formula I:

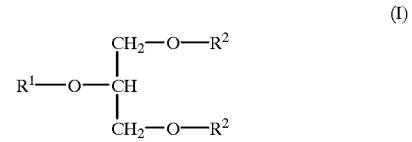

(I)

wherein R is a $C_{12}$–$C_{22}$ linear or branched alkyl or alkenyl group; and $R^1$ and $R^2$ are, each independently, hydrogen or an acyl moiety {—C(=O)—$R^3$} wherein $R^3$ is a linear or branched $C_1$–$C_{30}$ alkyl or alkenyl; and pharmaceutically-acceptable salts thereof, is disclosed. Nutritional supplements, dietary supplements and food additives comprising one or more substantially pure compounds of Formula I is also disclosed.

7 Claims, No Drawings

NUTRITIONAL SUPPLEMENTS FOR REPLENISHING PLASMALOGENS

FIELD OF THE INVENTION

The invention relates to nutritional supplements and methods of using them. More particularly, the invention relates to nutritional supplements which aid in the replenishment of plasmalogens.

1. Bibliography

Complete bibliographic citation for the references cited below are included in the "Bibliography" section, immediately preceding the claims. All of the references cited below are incorporated herein by reference in their entirety.

2. Description of the Prior Art

Glycerophospholipids and related glycerol-derived lipid analogs are ubiquitous compounds which are major constituents in mammalian cellular membranes. For instance, they are present in relatively large amounts in skin fibroblasts. As a class of compounds, these lipids share the common feature of a 3-carbon glycerol backbone. A wide range of physiologically important compounds, such as phosphatidic acid analogs, fatty acid and aldehyde glycerols, ether glycerol phospholipids, plasmalogens, and the like, are defined by the chemical side chains attached to the glycerol backbone. The side chains are linked to the glycerol backbone via several different types of bonds, including ester linkages, ether linkages, phosphoester linkages, and alk-1'-enylether linkages.

Ether glycerophospholipids bearing an alk-1'-enylether-linked substituent are given the trivial class name plasmalogens. Plasmalogens are generally thought to play an important, albeit undefined, role in cellular growth, maintenance, and apoptosis. For instance, it is thought that plasmalogens function as antioxidants in vivo . Reiss et al. (1997) showed in an in vitro model that the peroxidation of lipids is delayed in the presence of plasmalogens. The uncertainty of the role played by reactive oxygen intermediates, if any, in programmed cell death is summed up by Nunez and Clarke (1994), who note that "it is unclear whether reactive intermediates are required for apoptosis."

For an excellent review of the present scientific knowledge regarding ether phospholipids in biomembranes, see Paltauf (1994).

Decreased antioxidant status has been implicated in the aging process. Not only are dietary antioxidants, such as Vitamnin C and Vitamin E, decreased, but enzymes normally present to neutralize these oxygen radicals appear to be deficient as well. Enzymes such as superoxide dismutase, catalase and glutathione peroxidase appear to be produced in lesser quantities as the body ages. Most importantly, the levels of plasmalogens are significantly decreased with age.

Particularly helpful in understanding the general field to which the invention pertains is Paltauf's discussion of ether lipid biosynthesis and metabolism in mammalian cells. An interesting feature of the biosynthetic pathway is that two of the enzymes involved in the formation of an alkyl ether bond to the glycerol backbone, namely dihydroxyacetone phosphate acyltransferase (DHAP-AT) and alkyldihydroxyacetone phosphate synthase (alk-DHAP synthase) are located solely in the peroxisomes. Consequently, the biosynthetic pathway leading from dihydroxyacetone phosphate (DHAP) to glycerophospholipids is divided between cytosolic reactions (at both the initial and final stages of synthesis) and peroxisome-located reactions.

The metabolic pathway leading from DHAP to various glycerophospholipids, as described by Paltauf (1994), is summarized below.

DHAP from the cytoplasm is first imported into the peroxisome, where it then reacts with acyl CoA to yield a 1-acyl-3-hydroxyacetone phosphate. This first reaction is catalyzed by DHAP-AT. Enzymatic reaction with a primary alcohol (catalyzed by alkyl-DHAP-synthase) then yields the 1-alkylether-3-hydroxyacetone phosphate analog. Further reaction with NADPH causes reduction of the 2-position carbonyl into an alcohol. At this point, the 1-alkylether-2-hydroxyglycerol-3-phosphate intermediate is transported out of the peroxisome for further biosynthetic reactions in the cytoplasm or endoplasmic reticulum (ER). The biosynthetic reactions which occur solely within the peroxisome are summarized as follows:

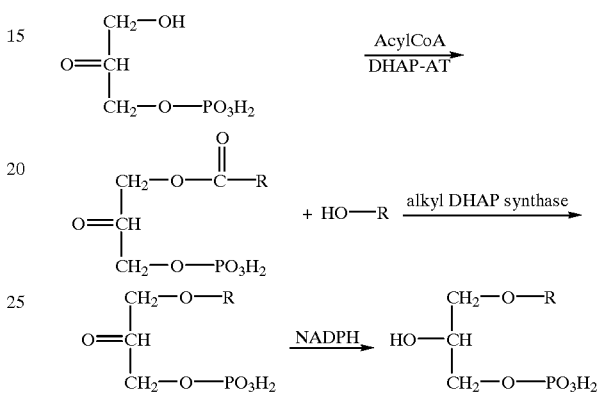

Outside of the peroxisome, plasmalogens are formed by the step-wise acylation of the 2-position carbonyl, amine functionalization of the 3-position orthophosphate (as with choline or ethanolamine), followed by enzymatic dehydrogenation of the 1-position alkylether side chain.

Paltauf notes that in peroxisomal disorders such as Zellweger's syndrome and rhizomelic chondrodysplasia punctata (RHCP), the impediment to the peroxisomal enzymatic reactions may be circumvented by providing to the either lipid-deficient cells a suitable precursor which can be used for plasmalogen synthesis in the ER. For instance, Paltauf notes that fibroblasts from healthy donors contain approximately 15% ethanolamine plasmalogen. However, supplying exogenous alkylglycerol to these normal cells has no effect on the plasmalogen content of the cells. In contrast, the reduced plasmalogen levels found in cultured fibroblasts of Zellweger's or RHCP patients can be elevated to almost normal levels if the cells are cultured in the presence of an alkylglycerol. (See also, Hennetter and Paltauf (1995).)

It must be noted, however, that very little is known about the ether lipid content of other tissues in patients suffering from peroxisomal disorders. See, for instance, Das et al. (1992). Das et al. note that chronic feeding of 1-O-octadecyl-sn-glycerol (batyl alcohol) to human patients suffering from peroxisomal disorders which result in a low tissue content of ether glycerolipids, results in increased plasmalogen content within their red blood cells (erythrocytes). Das et al. were interested in whether the oral administration of ether lipids to patients with peroxisomal disorders might increase the concentration of tissue ether lipids. Das et al. convincingly show that chronic oral administration of batyl alcohol to patients suffering from certain peroxisome dysfunction disorders results in a significant increase in red blood cell ethanolamine plasmalogen concentration. This leads Das et al. to conclude that the administration of oral ether lipids represents a "potential" treatment for patients with peroxisomal disorders.

This conclusion, however, must be treated with caution in that while Das et al. noted that the infant subjects described therein showed improved nutritional status, liver function, retinal pigmentation, and replenishment of deficient erythrocyte ethanolamine plasmalogen level by the feeding of ether lipids, Das et al. also conclude that it is not possible to separate these changes from the natural history of the untreated disease. For instance, Wander et al. (1986) have documented that plasmalogen levels in Zellweger's syndrome patients increase naturally as a function of age. It is hypothesized that this may be due to the intake of natural alkylglycerols present in food. Alkylglycerols and their mono- and diesters are found in fish oils, such as shark oil, and other foods. Horrocks (1972) estimates that the average adult consumes from 10–100 milligrams of batyl alcohol per day.

Das et al. also investigated the extent of incorporation of dietary ether lipids into tissue lipids by administering different precursors of the ether lipids, such as heptadecanoic acid, heptadecanol, 1-O-heptadecyl-sn-glycerol, and 3-O-heptadecyl-sn-glycerol, to young rats. Das et al.'s data indicate that natural glycerols are incorporated more readily than unnatural optical isomers. While the precursors were incorporated into various plasmalogens, the total plasmalogen content of the tissues tested did not increase. The relative incorporation rates of the various ether lipid precursors is reported by Das et al. to be as follows: 1-O-heptadecyl-sn-glycerol> heptadecanol>heptadecanoic acid>3-O-heptadecyl-sn-glycerol. This leads Das et al. to conclude that while most exogenous long chain either lipids are eventually incorporated into alkylglycerol ether lipids, the subsequent conversion of the alkylglycerol ether lipids into plasmalogens occurs only in those lipids containing a 1-alkyl side chain of between $C_{15}$ and $C_{19}$ which is fully saturated or mono-unsaturated.

It is against this background of uncertain biological functionality, that a number of patents describe the use of glycerol derivatives in the treatment of various disease states. For instance, Horrmann, U.S. Pat. Nos. 4,505,933 and 4,687,783, describes a treatment for multiple sclerosis and "shaking paralysis," respectively, by orally administering a linear, unsaturated fatty aldehyde or acid derivative to a patient. Specifically, the two Hörrmann patents describe the treatment of multiple sclerosis or "shaking paralysis" by orally administrating a mixture of 6-n-dodecenoic aldehyde, 8-n-hexadecenoic aldehyde, and 8-n-hexadecenoic acid, followed by further oral administration of 6,12-n-octadecadienoic aldehyde, 8,16-n-tetracosadienoic-2-hydroxy aldehyde, and 8,16-n-tetracosadienoic-2-hydroxy acid.

Chalmers et al., U.S. Pat. No. 3,294,639, describe the treatment of inflammatory diseases such as rheumatoid arthritis by administering chimyl, selachyl, or batyl alcohol to a patient. A treatment for asthma utilizing the same compounds is described by Brohult et al., U.S. Pat. No. 5,173,511. These compounds are 1-position monoethers of glycerol: chimyl alcohol is the hexadecyl monoether, selachyl alcohol the octadecenyl (i.e., oleyl) monoether, and batyl alcohol the octadecyl monoether. Synthesis of these compounds is well known in the art (see, for instance, Takaishi et al., U.S. Pat. No. 4,465,869 and UK Patent 1,029,610). In addition, mono- and di-esters of alkylglycerols are well-known in the art and their syntheses have been described {see, for example, Burgos et al. (1987); Hirth et al. (1982); and Hirth et al. (1983)}.

U.S. Pat. No. 5,731,354 entitled "TREATMENT FOR THE INHIBITION OF NEURO-DEGENERATIVE DISEASE STATES" describes a method of treating or inhibiting neurological disorders with batyl alcohol and congeners thereof.

In stark contrast to the clearly therapeutic aims of the aforementioned references, the present invention is specifically directed toward the use of the compounds of the present invention as mammalian nutritional supplements, dietary supplements and food additives for the replenishment of plasmalogens in mammalian cells.

It is apparent from the foregoing that a need exists for providing a nutrient to an individual, which upon consumption of the nutrient by the individual, directly or indirectly leads to the replenishment of plasmalogens in the individual during times when the individual's plasmalogen levels fall below normal.

SUMMARY OF THE INVENTION

The subject invention is drawn to a method of replenishing plasmalogens in mammals, thereby preventing, ameliorating, or treating nutritional deficiencies mediated in whole or in part by decreased plasmalogen levels. The method comprises treating mammals, including humans, with a plasmalogen-replenishing-effective amount of one or more compounds of Formula I:

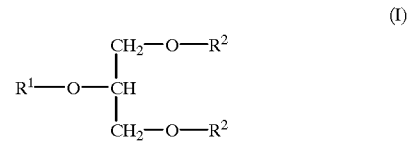

wherein R is a $C_{12}$–$C_{22}$ linear or branched alkyl or alkenyl group; and $R^1$ and $R^2$ are, independent of each other, hydrogen or an acyl moiety {—C(=O)—$R^3$} wherein $R^3$ is a linear or branched $C_1$–$C_{30}$ alkyl or alkenyl; and pharmaceutically-acceptable salts thereof.

Preferably, a compound of Formula I wherein R is selected from the group consisting of $C_{16}$ to $C_{18}$ linear or branched alkyl and $R^1$ and $R_2$ are hydrogen, pharmaceutically-acceptable salts thereof, or combinations thereof, is administered to the subject in need thereof. From among these compounds, it is most preferred that chimyl alcohol, batyl alcohol, and pharmaceutically-acceptable salts thereof, or combinations thereof, is administered to the subject.

Administration of the compounds of Formula I can be by any route, including oral, topical, parenteral, and rectal. Oral administration of the compounds is preferred.

As used herein, the term "subject" expressly includes human and non-human mammalian subjects.

As used herein, the term "nutritional" denotes that which is beneficially assimilated by the subject for the growth or the general health of tissues.

As used herein, the term "dietary" denotes that which is naturally a part of the subjects diet.

As used herein, the term "food additive" denotes a substantially-pure material which is added to food for a nutritional benefit.

As used herein, the term "food product" denotes a product intended for ingestion by a mammal, including humans, which has nutritional value.

As used herein, the term "pharmaceutically-acceptable" means a component which is suitable for use with humans and/or animals without undue side effects.

All isomers of the compounds of Formula I, including positional and optical isomers, mixtures thereof, racemates thereof, and enantiomerically enriched or purified forms thereof, are encompassed within the term "compounds of Formula I".

A principal aim and object of the present invention is to provide a nutritional supplement to mammals which utilizes one or more metabolic precursors of naturally-occurring lipid compounds or analogs thereof.

A further aim of the invention is to provide a method to replenish plasmalogens in cells.

A still further aim of the invention is to provide a food additive comprising one or more compounds of Formula I.

A distinct advantage of the present invention is that it provides an effective nutritional or food supplement to maintain or replenish the plasmalogen level in a mammalian recipient.

DETAILED DESCRIPTION OF THE INVENTION

It has been found that nutritional and dietary compositions containing compounds of Formula I are effective to replenish plasmalogens in mammals, including human beings. The subject compounds are metabolic precursors of plasmalogens which are believed to protect against the damaging effects of free radicals.

While expressly disavowing any limitation to a given mode of action, it is thought that the nutritional action of the present invention is accomplished by increasing the availability of metabolic precursors or suitable substrates for the biosynthesis of free radical-scavenging molecules, most notably plasmalogens. By providing cells with either suitable substrates for plasmalogen synthesis by normal routes, or by inducing alternative pathways for plasmalogen synthesis, it is believed that the cells are thereby enabled to circumvent real or potential deterioration. This protective effect is believed to result from an increase in the free radical-scavenging ability of the cells.

Consequently, the present invention provides a method of providing a nutritional supplement or food additive to prevent free radical-mediated cell degeneration in a host mammal which comprises administering to the mammal an nutritionally-effective amount of one or more compounds of Formula I or pharmaceutically-acceptable salts thereof.

I. The Active Ingredients

The active ingredients used in the above-described method are $C_{12}$ to $C_{22}$ alkyl mon-ethers of glycerol and their mono- and di-ester derivatives. The compounds are known and several methods for their preparation are described in the chemical literature. As noted above, all positional and optical isomers of the compounds of Formula I, including racemic mixtures, pure or enriched enantiomeric forms, and mixtures thereof, are within the scope of the invention.

From among the compounds of Formula I, the preferred compounds for use in the present invention are the compounds wherein R is a $C_{16}$ to $C_{18}$ linear or branched alkyl group. Chimyl and batyl alcohol are most preferred. The preferred pharmaceutically-acceptable salts of the compounds of Formula I are mono or di-substituted basic salts such as sodium, potassium, and calcium salts.

When hydroxy is evident in the Formula I compound, the Formula I compound may exist in the form of a basic pharmaceutically-acceptable salt. As used herein, the term "pharmaceutically-acceptable salts" means any salt conventionally used in the formulation and administration of foodstuffs, nutritional supplements and other dietary preparations. This term encompasses mono- and di-substituted basic salts of sodium, potassium, calcium, and the like of. The foregoing list is exemplary, not exclusive. A large number of salts acceptable for dietary administration are known to those of skill in the art. The salts of the invention are made by conventional methods well-known to those in the art.

II. Routes of Administration and Dosage

Dietary compositions of the present invention comprise one or more nutritionally-effective compounds, i.e. one or more Formula I compounds, pharmaceutically-acceptable salts thereof, or combinations thereof, together with an acceptable carrier. The Formula I compounds may also be used as additives to other foodstuffs. The carrier must be pharmaceutically-acceptable in the sense of being compatible with the other ingredients of the formulation and not deleterious to the recipient thereof.

The formulations include those suitable for oral, topical, or parenteral (including subcutaneous, intramuscular and intravenous) administration.

The formulations may be manufactured in unit dosage form and may be prepared by any of the methods well-known in the art of the formulation of foods. All methods include the step of bringing the active compound into association with a carrier and one or more optional accessory ingredients. In general, the formulations are prepared by uniformly and intimately bringing the active compound into association with a liquid or solid carrier and then, if necessary, shaping the product into desired unit dosage form.

The in vivo dosage in humans and other mammals depends largely upon the age and general health of the patient being treated. Determining the optimum dosage for any given mammal is essentially an empirical and ongoing process. Replenishment of plasmalogens in infants and children may optimally require more (or less) aggressive nutritional considerations than in older patients.

In mammalian subjects, the compounds of Formula I are preferably administered orally in combination with a suitable inert liquid or solid orally-acceptable carrier. Such carriers are well known in the art. Formulations of the present invention suitable for oral administration include discrete units such as capsules, cachets, tablets, boluses or lozenges; each containing a predetermined amount of the nutritionally-effective compound; as a powder or a granular form; or in liquid form.

Tablets are made by compression or molding, optionally with one or more accessory ingredients. Compressed tablets are prepared by compressing the active compound in a free-flowing form, e.g., a powder or granules, optionally mixed with accessory ingredients, e.g., binders, lubricants, inert diluents, surface active or dispersing agents, using conventional tabletting machinery. Molded tablets may be made by molding a mixture of the powdered active compound with an suitable carrier, again using conventional and well-known molding equipment.

Formulations suitable for parenteral administration comprises a pre-measured concentrated solution or solid formulation containing a compound of Formula I, which upon dilution with an appropriate solvent yields a solution suitable for parenteral administration.

Another useful formulation for parenteral administration comprises a pre-measured concentrated solution or solid formulation containing a compound of Formula I, which upon dilution with an appropriate solvent yields a solution suitable for parenteral administration.

In addition to the aforementioned ingredients, the formulations of this invention may further include one or more optional accessory ingredient(s) utilized in the art of dietary formulations, e.g., diluents, buffers, flavoring agents, colorants, binders, surface active agents, thickeners, lubricants, suspending agents, preservatives (including antioxidants) and the like.

A suitable effective dose for most conditions ranges from about 1 mg/kg body weight to about 10 g/kg body weight per day, and is preferably in the range of from about 100 to about 500 mg/kg body weight per day (calculated as the non-salt form). The total daily dose may be given as a single dose, multiple doses, e.g., two to six times per day, or by intravenous infusion for a selected duration. Dosages above or below the above-cited ranges are within the scope of the invention and such dosages may be administered to individual subject if the circumstances so dictate.

For example, in a 75 kg mammal, a typical daily dosage might fall with the range of from about 100 mg to about 100 g per day. If discrete multiple doses are indicated, treatment might typically comprise 4 equal fractional doses given at 8 hour intervals to supply the total daily dosage.

III. Nutritional and Dietary Supplements

In general, heavy physical exercise and disease conditions may require the intake of considerable quantiites of vitamins, minerals and nutritional supplements apart from those available in the normal diet. Nutritional supplements are important primarily for individuals who have inadequate diets or a reduced ability to absorb or utilize the nutrients, especially the elderly. Typically, older individuals are less able to utilize nutrients from foods and are ill more often than younger individuals.

The added benefits of taking nutritional and dietary supplements to maintain health and protect against disease and illness is currently recognized. Antioxidants, such as Vitamin E and Vitamin C, for instance, are taken by many individuals to help neutralize free radicals and other reactive oxygen species. Free radicals are unstable molecules that damage cell structures. Examples of endogenously produced free radicals are superoxide anion, hydrogen peroxide and alkoxy radicals. These ever-present molecules, which are a natural consequence of aerobic metabolism, can also be created by illness, smoking, heat, radiation, alcohol and certain pollutants. The damaging effects of free radicals are combated by antioxidants.

Administration of an amount of one or more compounds of Formula I, either neat, or (preferably) in combination with a carrier, replenishes plasmalogens. Such a nutritional composition is taken as needed or on a daily basis to maximize their effectiveness.

The subject invention thus provides a method of replenishing plasmalogens which comprises administering pharmaceutically-acceptable amounts of one or more compounds of Formula I or pharmaceutically-acceptable salts thereof.

IV. Nutritional System

With respect to the foregoing discussion involving the administration of compounds of Formula I as nutritional supplements, one or more compounds of Formula I can also be administered as part of a nutritional system. The term "nutritional system" as used herein means a formulation comprised of a mixture of vitamins, minerals and other nutritional supplements. A nutritional system comprising one or more compounds of Formula I is particularly efficacious for the geriatric population. The present invention encompasses nutritional systems comprising one or more compounds of Formula I in combination with vitamins, such as Vitamin A, Vitamin C, Vitamin D, Vitamin E and the like, and minerals, such as calcium salts, magnesium salts, iron complexes and the like, and other nutritional supplements, such as essential amino acids, sugars, carbohydrates and the like.

The subject invention thus provides a method of replenishing plasmalogens, to combat the damaging effect of free radicals and to normalize the amount of these necessary components of cell membranes, which comprises administering nutritionally-effective amounts of one or more compounds of Formula I or pharmaceutically-acceptable salts thereof as part of a nutritional system.

V. Food Additives

Foodstuffs are often "fortified" with vitamins, minerals and nutritional supplements to enhance the nutritional value of the foodstuff. Nutritionals, such as compounds of Formula I, can also be added in substantially pure form to foodstuffs.

The food additive is comprised of an amount of one or more compounds of Formula I in an effective amount to replenish plasmalogens through the diet.

EXAMPLES

The Examples are included herein solely to illustrate, and not to limit, the scope and utility of the present invention.

Example 1

Nutritional Tablets

This is an illustrative example of tablets containing the following ingredients which may be prepared in the conventional manner:

| Ingredients | Per Tablet (mg) |
| --- | --- |
| Formula I compound | 50–100 |
| Lactose | 70 |
| Maize Starch | 70 |
| Polyvinylpyrrolidine | 5 |
| Magnesium Stearate | 5 |
| Tablet Weight | 200–250 |

Example 2

Nutritional Capsules

An illustrative example of capsules containing the following ingredients which may be prepared in a conventional manner:

| Ingredients | Per Capsule (mg) |
| --- | --- |
| Formula I compound | 50 |
| Lactose | 450 |

Example 3

Nutritional Elixir

An illustrative example of elixirs containing the following ingredients which may be prepared in a conventional manner:

| Ingredients | Per Dose (mg) |
|---|---|
| Formula I compound | 100 |
| Dexpanthenol | 10 |
| Niacinamide | 40 |
| pyridoxine hydrochloride | 4 |
| Cyanocobalamin | 0.000012 |
| Folic Acid | 1 |
| Iron polysaccharide complex | 4 |
| Zinc Sulfate | 15 |
| Manganese Sulfate | 4 |
| Alcohol | 42 |
| Elixir Weight | 220 |

Example 4

Nutritional Liquid for Intravenous or Intraperitoneal Administration

An illustrative example of liquids containing the following ingredients which may be prepared in a conventional manner:

| Ingredients | Per Dose (g) |
|---|---|
| Formula I compound | 5 |
| saline | 10 |
| propylene glycol | 85 |
| Liquid Weight | 100 g |

Example 5

Nutritional System for Geriatrics

An illustrative example of a nutritional system specifically formulated for administration to elderly humans containing the following ingredients combined into a tablet which may be prepared in a conventional manner:

| Ingredients | Per Tablet (mg) |
|---|---|
| Formula I compound | 100 |
| DL-α-Tocopheryl Acetate | 30 |
| Vitamin A Acetate | 1.7 |
| Ascorbic Acid | 500 |
| Thiamin Mononitrate | 20 |
| Riboflavin | 20 |
| Niacinamide | 100 |
| Pyroxidine Hydrochloride | 25 |
| Biotin | 0.15 |
| Calcium Pantothenate | 25 |
| Folic Acid | 0.8 |
| Cyanocobalamine | 0.0005 |
| Ferrous Fumarate | 27 |
| Chromium Nitrate | 0.1 |
| Magnesium Oxide | 50 |
| Manganese Dioxide | 5 |
| Cupric Oxide | 3 |
| Zinc Oxide | 22.5 |
| carnauba wax | 30 |
| ethylcellulose | 20 |
| ethyl vanillin | 20 |
| hydroxypropyl methylcellulose | 20 |
| magnesium stearate | 10 |
| povidone | 5 |
| triacetin | 5 |
| stearic acid | 25 |
| silicon dioxide | 34.7495 |
| Tablet Weight | 1200 |

BIBLIOGRAPHY

Amon, U.; von Stebut, E.; Ramachers, U.; and Wolff, H. H. (1993); Influence of protein kinase C activation on basophils from patients with atopic dermatitis in comparison with nonatopic controls, *Clin. Lab. Invest.*, 186:109–112.

Burgos, C. E.; Ayer, D. E.; and Johnson, A. R. (1987); A New, Aysymmetric Synthesis of Lipids and Phospholipids, *J. Org. Chem.* 52: 4973–4977.

Das et al. (1992); Dietary Ether Lipid Incorporation Into Tissue Plasmalogens of Humans and Rodents, *LIPIDS*, 27(6): 401–405.

Hermetter, A. and Paltauf, F. (1995); in "Phospholipids: Characterization, Metabolism, and Novel Biological Applications," Cevc, G., Paltauf, F., Eds.; pp. 260–273: AOCS Press, Champaign, Ill.

Hirth, G. V. and Barner, R. (1982); Herstuellung von 1-O-Octadecyl-2-O-acetyl-sn-glyceryl-3-phosphorylcholin ('Platelet Activating Factor'), des Enantiomeren sowie einiger analoger Verbindungen, *Helv. Chim. Acta* 65: 1059–1084.

Hirth, G. V.; Saroka, H.; Bannwarth, W.; and Barner, R.; (1983); Herstellung von 2-O-Acetyl-1-O-[(Z)-9-octadecenyl]-sn-glyceryl-3-phosphorylcholin («Oleyl-PAF»), des Enantiomeren sowie einiger analoger, ungesaittigter Verbindungen, *Helv. Chim. Acta* 66: 1210–1240.

Horrocks (1972); in "Ether Lipids: Chemistry and Biology," Snyder, F. Ed., pp. 177–272.

Nunez and Clarke (1994); "The Bcl-2 Family of Proteins: Regulators of Cell Death and Survival," *Trends in Cell Biology*, 4:399–403.

Paltauf, F. (1994); Ether lipids in biomembranes, *Chemistry and Physics of Lipids*, 74:101–139.

Reiss, D.; Beyer, K.; and Englemann, B. (1997); Delayed oxidative degradation of polyunsaturated diacyl phospholipids in the presence of plasmalogen phospholipids in vitro, *Biochem J.* 323: 807–814.

Wanders et al. (1986); *J. Inher. Metab. Dis.*, 9:335–342.

What is claimed is:

1. A method of reducing a dietary deficiency in a mammal suffering from a dietary deficiency comprising administering to the mammal a dietary-enhancing-effective amount of one or more substantially pure compounds of Formula I

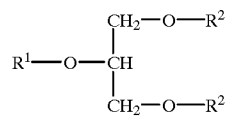
(I)

wherein R is a $C_{12}$–$C_{22}$ linear or branched alkyl or alkenyl group;

and $R^1$ and $R^2$ are, each independently, hydrogen or acyl moiety {—C(=O)$R^3$} wherein $R^3$ is a linear or branched $C_1$–$C_{30}$ alkyl or alkenyl; and pharmaceutically-acceptable salts thereof.

2. The method of claim 1 wherein $R^1$ and $R^2$ are hydrogen.

3. The method of claim 1 wherein the compound of Formula I is selected from the group consisting of chimyl alcohol, batyl alcohol, selachyl alcohol, pharmaceutically-acceptable salts thereof, and combinations thereof.

4. The method of claim 1 wherein the compound of Formula I is administered orally.

5. The method of claim 1 wherein the compound of Formula I is administered parenterally.

6. The method of claim 1 wherein the mammal is a human.

7. The method of claim 1 wherein the mammal is an elderly human.

* * * * *